United States Patent [19]

Roberts et al.

[11] Patent Number: 5,143,212
[45] Date of Patent: Sep. 1, 1992

[54] GEMSTONE COLOR COMMUNICATION KITS

[75] Inventors: Kenneth G. Roberts; Elaine E. Roberts, both of Warwick, R.I.

[73] Assignee: K. G. Roberts & Associates, Inc., East Greenwich, R.I.

[21] Appl. No.: 680,671

[22] Filed: Apr. 3, 1991

Related U.S. Application Data

[63] Continuation-in-part of Ser. No. 417,685, Oct. 5, 1989.

[51] Int. Cl.$^5$ .................................................. G01J 3/46
[52] U.S. Cl. ....................................... 206/223; 206/81; 206/457; 434/99; 434/386; 356/30
[58] Field of Search ................. 63/12, 13, 14.1, 20, 63/28, 26; 356/30; 434/98, 99, 100, 386; 206/457, 459, 223, 81, 6.1

[56] References Cited

U.S. PATENT DOCUMENTS

| | | |
|---|---|---|
| D. 61,820 | 1/1923 | Biro . |
| 256,640 | 4/1882 | Clark . |
| D. 257,023 | 9/1980 | Barr . |
| 521,192 | 6/1894 | Tilford et al. ............ 63/14.1 |
| 800,968 | 10/1905 | Anderson . |
| 824,374 | 6/1906 | Munsell . |
| 884,968 | 4/1908 | Wood . |
| 993,797 | 5/1911 | Sale . |
| 1,092,587 | 4/1914 | Meyers ................... 63/28 |
| 1,234,974 | 7/1917 | Uhl . |
| 1,385,691 | 7/1921 | Knaus ................... 63/20 X |
| 1,480,486 | 1/1924 | Allen ..................... 356/421 |
| 1,597,830 | 8/1926 | Rueger . |
| 1,612,791 | 1/1927 | Ames et al. ............... 356/422 |
| 1,617,024 | 2/1927 | Munsell et al. . |
| 1,709,937 | 4/1929 | Everard ............... 434/386 X |
| 2,007,264 | 7/1935 | Allen . |
| 2,230,585 | 2/1941 | Canter . |
| 2,270,210 | 1/1942 | Barbieri .................... 63/32 |
| 2,353,744 | 7/1944 | Meyer ..................... 117/66 |
| 3,089,584 | 5/1963 | King ....................... 206/1.8 |
| 3,474,546 | 10/1969 | Wedlake ................... 434/98 |
| 3,746,161 | 7/1973 | Jones ....................... 206/72 |
| 3,832,070 | 8/1974 | Cox ........................ 356/209 |
| 3,912,521 | 10/1975 | Cline et al. ............... 106/42 |
| 3,944,368 | 3/1976 | Beesley .................... 356/30 |
| 3,975,097 | 8/1976 | Minto ...................... 356/30 |
| 3,997,686 | 12/1976 | McClure ...................... 63/1 |
| 4,043,675 | 8/1977 | Guennel et al. ............ 356/191 |
| 4,083,352 | 4/1978 | Andrychuk .................. 63/32 |
| 4,106,221 | 8/1978 | Selon ...................... 434/386 |
| 4,243,626 | 1/1981 | Prete ...................... 264/153 |
| 4,266,871 | 5/1981 | Ritzi ....................... 356/30 |
| 4,295,347 | 10/1981 | Visconti .................... 63/32 |
| 4,461,568 | 7/1984 | Welbourn et al. ........... 356/30 |
| 4,482,245 | 11/1984 | Makabe et al. ............. 356/30 |
| 4,490,440 | 12/1984 | Reber ..................... 428/620 |
| 4,508,449 | 4/1985 | Okazaki .................... 356/30 |
| 4,527,895 | 7/1985 | Rubin ...................... 356/30 |
| 4,534,644 | 8/1985 | Beesley .................... 356/30 |
| 4,591,215 | 5/1986 | Robbins ................. 312/234.3 |
| 4,604,329 | 8/1986 | Reber ..................... 428/620 |
| 4,703,020 | 10/1987 | Nakano et al. ............. 501/86 |
| 4,819,453 | 4/1989 | McNamara ................... 63/28 |
| 4,827,575 | 5/1989 | Delaney ..................... 63/3 |
| 4,835,023 | 5/1989 | Taniguchi et al. .......... 428/15 |
| 4,887,906 | 12/1989 | Koehler ................... 356/402 |
| 4,920,991 | 5/1990 | Shibahashi et al. ......... 132/73 |
| 5,005,971 | 4/1991 | Davis ...................... 356/30 |

FOREIGN PATENT DOCUMENTS

2036360 6/1980 United Kingdom .
2155199 9/1985 United Kingdom .

OTHER PUBLICATIONS

Modern Jeweler, "In Living Color" by D. Federman, Feb., 1991.
National Jeweler, "GemstoneNews" by A. Joy et al, Mar., 1991.

*Primary Examiner*—Paul T. Sewell
*Assistant Examiner*—Jacob K. Ackun, Jr.
*Attorney, Agent, or Firm*—Nixon & Vanderhye

[57] ABSTRACT

Kits adapted to allow subjective evaluation and communication of gemstones include a number of simulated gemstones which are arranged in an ordered set according to their respective hue, chroma and/or value characteristics. Each of the simulated gemstones includes a multifaceted gemstone body portion (which preferably closely resembles a brilliant cut diamond) and a handle portion radially extending from the body portion. The handle portion allows the multifaceted body portion to be manipulated in ambient light conditions so the color can be adequately observed. The simulated gemstones are formed of a molded plastics material which exhibits unique color hue, chroma and value characteristics. The hue, chroma and value characteristics may be varied within an ordered set of the simulated gemstones so as to achieve a close color match with natural gemstones. These ordered sets of simulated gemstones may thus be displayed in respective trays. Thus, the kits of this invention may be provided in multiple trays, with each tray being dedicated to a particular color set of the simulated gemstones.

24 Claims, 1 Drawing Sheet

GEMSTONE COLOR COMMUNICATION KITS

RELATED APPLICATIONS

This application is a continuation-in-part of copending U.S. Design patent application Ser. No. 07/417,685 filed on Oct. 5, 1989, in the name of the same inventors as this application and entitled "Simulated Gemstone Display Device", the entire content of which is expressly incorporated hereinto by reference.

FIELD OF THE INVENTION

The present invention relates generally to simulated gemstone kits that may be employed usefully in the field of gemology so as to assist in the subjective evaluation of color characteristics of precious and semi-precious gemstones (e.g., so as to match and/or appraise the same) and to then communicate such subjectively evaluated color to a third party (e.g., a gem supplier, retail jeweler, consumer or gemology student).

BACKGROUND AND SUMMARY OF THE INVENTION

Color systems, such as the Munsell (see U.S. Pat. No. 824,374, incorporated fully hereinto by reference) and C.I.E. (Commission Internationale de l'Eclairage) systems, which use the three color coordinates of hue, intensity of saturation or chroma (hereinafter simply referred to as "chroma") and darkness/lightness value (hereinafter simply referred to as "value") are notoriously well known. In this connection, these color coordinate systems enable an essentially three-dimensional color model to be constructed whereby the characteristics of any color may be identified using its unique hue, chroma and value coordinates.

As may be appreciated, a three-dimensional "solid" color model is unwieldy since it is usually difficult to access and use the colors in the model's interior—that is, those colors closely adjacent to the value scale. Thus, various proposals have been made whereby three-dimensional color models are constructed which allow the interior colors in the model to be accessed. In this regard, please see U.S. Pat. No. 1,480,486 to Allen and U.S. Pat. No. 3,474,546 to Wedlake.

Other "two-dimensional" color systems have also been proposed as evidenced by U.S. Pat. No. 1,597,830 to Rueger, U.S. Pat. No. 1,612,791 to Ames et al, U.S. Pat. No. 1,617,024 to Munsell et al, and U.S. Pat. No. 2,007,264 to Allen. In essence, each of these systems provide for an organized two-dimensional arrangement of color patches printed upon an underlying substrate.

More recently, a color grading system for gemstones has been proposed in U.S. Pat. No. 4,527,895 to Rubin whereby so-called color-masking charts (each comprised of a series of sample achromatic color swatches printed upon a transparent flexible film substrate and arranged in increasing amounts of the achromatic color) may be overlaid with chromatic color charts (each comprised of a series of sample chromatic color swatches printed upon a transparent flexible film substrate in increasing intensities of color saturation) so as to closely approximate the color characteristics of particular gemstones.

However, since the system disclosed in the Rubin '895 patent necessarily depends upon color swatches printed upon a transparent substrate, the swatch is exposed to physical abrasion during use such that its integrity and/or quality may degrade over time. As a result, the accuracy of color matches using such a system will likewise degrade over time. In addition, the printed swatches often lack the clarity and/or intensity of color that is intended to be matched (i.e., since the color is presented "two-dimensionally" because of the thin films upon which the color swatches are printed) so that oftentimes only a close approximation of the actual color characteristics of the gemstones may be achieved.

Thus, it is towards providing more faithful and convenient gemstone color communication kits which the present invention is directed.

Broadly, the present invention is embodied in kits which assist in the subjective evaluation of color characteristics of precious and semi-precious gemstones, and which allow the evaluated color to then be objectively communicated to third parties. Once the color characteristics of a particular gemstone have been determined, for example, a matched gemstone having comparable color characteristics may be selected by a gem supplier who has not inspected the gemstone that was evaluated using the kits of this invention.

The present invention is preferably embodied in kit form which include an ordered set comprised of a number of simulated gemstones. Each of the simulated gemstones includes a multifaceted gemstone body portion (which preferably closely resembles a brilliant cut gemstone having 58 facets) and a handle portion radially extending from the body portion. The handle portion thus allows the multifaceted body portion to be manipulated in ambient light conditions so that its color characteristics can adequately be observed.

Each of the simulated gemstones is formed of a molded plastics material which exhibits unique color hue, chroma and value characteristics. Thus, within each hue, the chroma and value characteristics may be varied within an ordered set so as to achieve a close color match with natural gemstones.

The ordered sets of simulated gemstones are most preferably displayed in respective trays. Thus, the kits of this invention may be provided in multiple trays, with each tray being dedicated to a particular color set of simulated gemstones. The individual trays according to this invention will include an opposing pair of recesses which are sized and configured to accept therewithin the gemstone body portion and an opposing terminal end of the handle portion. The tray also includes a fulcrum surface against which a corresponding portion of the handle portion bears so that the gemstone body portion may be pivoted upwardly from its corresponding recess in response to downward pressure being applied against the handle portion's terminal end.

Further aspects and advantages of this invention will become more clear after careful consideration is given to the following detailed description thereof.

BRIEF DESCRIPTION OF THE ACCOMPANYING DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1A:
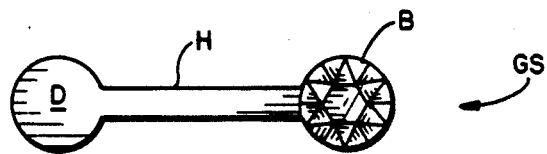
FIGURES 1a and 1b are plan and elevation views, respectively, of a simulated gemstone according to the present invention.
Figure 1B:
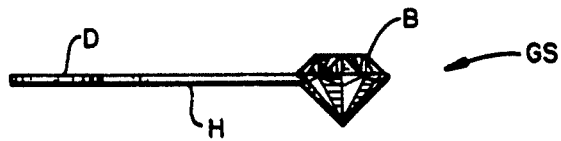

The kits 100 according to this invention will include simulated gemstones GS as depicted in FIGURES 1a and 1b. As is shown, each of the gemstones GS is in the form of a unitary structure which is preferably injection molded from a suitable essentially transparent resin material (e.g., methylmethacrylate, refractive index=1.49). The gemstones GS each include a gemstone body portion B which simulates a so-called modern brilliant cut stone (i.e., having 58 facets), and a handle portion H radially extending from the gemstone body portion B. The handle portion H permits the gemstone GS to be manually manipulated in the ambient light conditions so as to observe the light transmission (and hence the color brilliance) through the gemstone body portion B.

The handle portion H terminates in a disc-like member D. Since, the gemstones GS are in the form of a unitary structure, the particular color of the disc-like portion D will be the same as the color of the gemstone body portion B. However, since the gemstone body portion B is multifaceted, the light transmission therethrough will be diffused differently so that a somewhat different color will be perceived as compared to the color of the essentially planar disc-like portion D. As a result, the color "brilliance" of precious and semi-precious gemstones can be more faithfully evaluated using the kit 100 shown in FIGS. 2 and 3.

Figure 2:
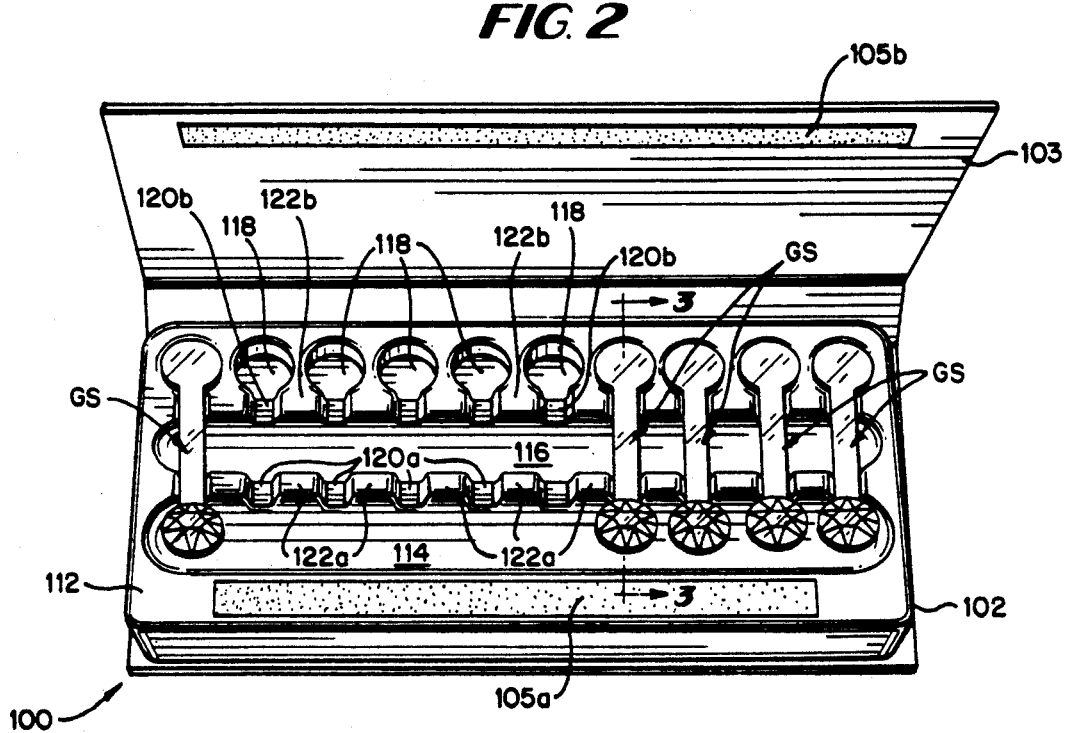
FIG. 2 is a perspective view of the gemstone color communication kit according to this invention.
Figure 3:
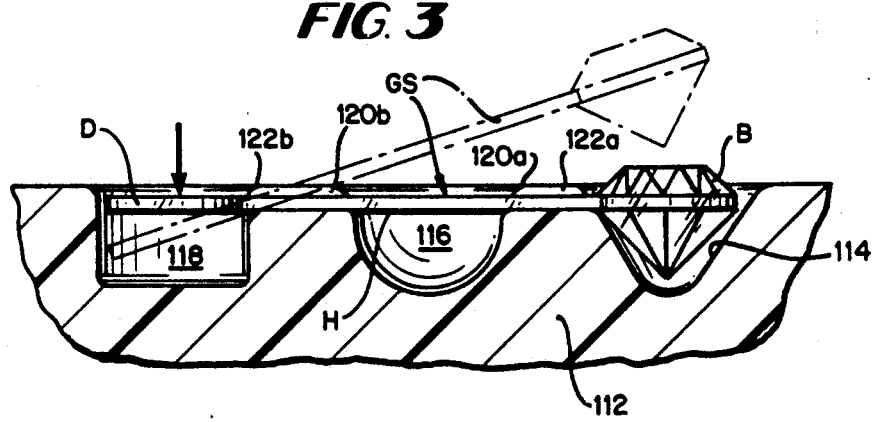
FIG. 3 is an enlarged cross-sectional view of the gemstone color communication kit shown in FIG. 2 as taken along line 3—3 therein.

The kit 100 shown in FIGS. 2 and 3 is especially adapted to assist gemologists in evaluating the color of precious and semi-precious gemstones. In this connection, the kit 100 includes a carrying tray 102 which holds a number of simulated gemstones GS in a selected ordered arrangement. For example, the gemstones GS may be arranged in an ordered chromatic hue series in which the chroma and/or value coordinates for each respective gemstone GS in the tray 102 are varied. In this connection, the kit 100 shown in FIG. 7 is depicted as having only a single row of gemstones GS in a single tray 102. However, numerous rows of gemstones GS and/or several trays 102 may be provided to suit the particular needs of the end-user.

In especially preferred embodiments of this invention, the kit 100 will include an ordered set of 324 simulated gemstones GS representing 31 hues of color, but each with different degrees of value and chroma. Each of the gemstones GS may thus bear a unique and identifiable number within a value and chroma grid for each color hue and may be arranged in one or more trays in their numerical order within such value and chroma grid. The kit 100 may also include a cross-reference to standardized color coordinate systems (e.g., the Munsell and/or CIE L*a*b color coordinate systems) which enable users of the kit 100 to communicate objectively with third parties not having a similar kit 100 available.

As is seen in FIG. 2, the tray 102 has a cover 103 which provides a protective lid over the the gemstones GS when closed, but may be opened to expose the gemstones GS when desired. The cover 103 may releasably be closed by any suitable fastener system, for example snaps, loop and pile fabric fasteners 105a, 105b (e.g., Velcro ® brand fasteners), or the like.

The tray 102 also has a bed 112, in which a head recess 114 and a central recess 116 are formed. As is perhaps better seen in FIG. 3, the head recess 114 is sized and configured to accept the gemstone body portion B therewithin. The disc-like portion D, on the other hand is received within a respective one of the appropriately disc-like configured pockets 118 formed rearwardly of the central recess 116. The handle portion H is received in channel recesses 120a, 120b formed in the respective forward and rearward support bridges 122a, 122b provided in the bed 112. As a result, the individual simulated gemstones GS are disposed transversely relative to the elongated dimension of the recesses 114 and 116.

Although a user may easily remove one of the gemstones GS from the bed 112 when an adjacent gemstone has already been removed therefrom by simply inserting a finger into the recess 116 and grasping the handle portion H, some difficulties may be encountered when gemstones GS are adjacent to that one which is desired to be removed. However, a user may simply press downwardly against the disc-like portion D as shown by the arrow in FIG. 3. Since the pocket 118 is generally cylindrical and thereby sufficiently deep so that the disc-like portion D is maintained in vertically spaced relation to the bottom wall of pocket 118, downward pressure against the disc-like portion D will cause the rearward bridge 122b to serve as a fulcrum to enable the handle portion H to pivot thereagainst. As a result, the gemstone body portion B will be raised upwardly out of the recess 114 as shown by the phantom line depiction in FIG. 3 to enable a user to grasp and remove the entire gemstone GS from the case bed 112.

As will now be appreciated, the kits 100 according to the present invention are especially adapted to evaluating and objectively communicating the color characteristics of precious and semi-precious gemstones. Thus, a somewhat "coarse" color comparison with a precious or semi-precious gemstone may be made by comparing its color to the color of the disc-like portion D associated with the simulated gemstones GS in kit 100. That gemstone GS may then be removed and manually manipulated in ambient light conditions so that a "fine" color comparison may be made with the precious or semi-precious gemstone by viewing the light transmission through the multifaceted gemstone body portion B. In this manner, a more reliable color evaluation with the precious or semi-precious gemstone may be achieved. The evaluated color may then be objectively communicated to others by means of the number associated with each of the gemstones GS and/or by means of standardized color coordinate systems.

Thus, while the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A kit for assisting in color evaluations of transparent natural colored gemstones comprising:
    a number of colored simulated gemstones formed of a molded transparent colored plastics material, said simulated gemstones each having a gemstone body portion and a handle portion which radially projects from said gemstone body portion; wherein said gemstone body and handle portions of said simulated gemstones are in the form of a one-piece unitary structure and thereby have the same selected color characteristic in terms of color hue, chroma and/or value that is different from the color characteristics of others of said simulated gemstones in the kit, but wherein said gemstone body and handle portions are structurally configured to diffuse light differently so that a somewhat different color attributable to said gemstone body portion is perceptible as compared to the perceptible color which is attributable to said handle portion; and wherein said handle portions allow each said simulated to be grasped manually so as to permit manipulation of the simulated gemstone in ambient light conditions for purposes of comparing the color characteristics of said simulated gemstone with a natural colored gemstone having similar color characteristics such that a relatively course color comparison may be made between the natural colored gemstone and said handle portion of said simulated gemstone, and a relatively fine color comparison may be made between the natural gemstone and said gemstone body portion of said simulated gemstone.

2. A kit as in claim 1, wherein said gemstone body portion is multifaceted to resemble a brilliant cut natural gemstone.

3. A kit as in claim 1, wherein said simulated gemstones are molded from a methylmethacrylate resin having an index of refraction of about 1.49.

4. The combination comprising at least one simulated gemstone, and a tray for said gemstone, wherein said simulated gemstone includes a gemstone body portion and a handle portion with opposing ends, one end of said handle portion being rigidly connected to said gemstone body portion so that said handle portion radially extends therefrom; and wherein said tray includes means for receiving and positionally retaining said simulated gemstone within said tray which includes;
(i) an opposing pair of recesses, one of said recesses being sized and configured to accept therewithin said gemstone body portion so as to positionally retain the same, and the other of said recesses being in registry with the other of said opposing ends of said handle portion such that said other end of said handle portion may be pushed towards a bottom of said other recess;
(ii) means establishing a fulcrum surface against which a corresponding portion of said handle portion bears, said fulcrum surface for assisting in the upward pivoting of said gemstone body portion relative to said one recess in which it is received in response to said other end of said handle member being manually pushed into said other recess, whereby said gemstone body portion may be grasped and removed from said tray.

5. The combination as in claim 4, further comprising an intermediate recess provided between said one and other recesses, said intermediate recess being sized and configured to allow a user's finger to be inserted therein and thereby grasp said handle portion.

6. The combination as in claim 4, wherein said other opposing end of said handle portion includes a disc-like member, and wherein said other of said recesses is in the form of a cylindrical pocket.

7. The combination as in claim 6, wherein said simulated gemstone is a unitary structure consisting essentially of molded methylmethacrylate resin having an index of refraction of about 1.49.

8. The combination as in claim 4, wherein said tray includes a removable cover for covering said at least one gemstone positionally retained therewithin.

9. The combination as in claim 4, wherein a number of said simulated gemstones are arranged within said tray in the form of an ordered color series.

10. A simulated gemstone for assisting in color evaluations of natural colored gemstones comprising:
a multifaceted gemstone body portion, and a handle portion, said gemstone body and handle portions being a one-piece unitary structure formed of a molded transparent colored plastics material thereby having the same selected color characteristic in terms of color hue, chroma and/or value; wherein said gemstone body and handle portions are structurally configured to diffuse light differently so that a somewhat different color attributable to said gemstone body portion is perceptible as compared to the perceptible color which is attributable to said handle portion; and wherein said handle portion radially extends from said gemstone body portion to allow the gemstone body and handle portions to be manipulated in ambient light conditions for purposes of comparing the color characteristics of said simulated gemstone with a natural colored gemstone having similar color characteristics such that a relatively course color comparison may be made between the natural colored gemstone and said handle portion of said simulated gemstone, and a relatively fine color comparison may be made between the natural gemstone and said gemstone body portion of said simulated gemstone.

11. A simulated gemstone as in claim 10, wherein said gemstone body portion resembles a brilliant cut natural gemstone.

12. A simulated gemstone as in claim 1 or 11, wherein said handle portion terminates in a disc-like member.

13. A simulated gemstone as in claim 12, wherein said one-piece unitary structure includes said gemstone body and handle portions and said disc-like member.

14. A simulated gemstone as in claim 13, wherein said one-piece structure is molded from a methacrylic resin having an index of refraction of about 1.49.

15. A simulated gemstone as in claim 1 or 10, wherein said handle portion is substantially planar.

16. A kit for assisting in color evaluations of natural colored gemstones comprising a tray, and a number of simulated gemstones organized with said tray in the form of an ordered color series, wherein each said gemstone includes:
a multifaceted gemstone body portion, and a handle portion, said gemstone body and handle portions being a one-piece unitary structure formed of a molded transparent colored plastics material thereby having the same selected color characteristic in terms of color hue, chroma and/or value; wherein said gemstone body and handle portions are structurally configured to diffuse light differently so that a somewhat different color attributable to said gemstone body portion is perceptible as compared to the perceptible color which is attributable to said handle portion; and wherein said handle portion radially extends from said gemstone body portion to allow the gemstone body and handle portions to be manipulated in ambient light conditions for purposes of comparing the color characteristics of said simulated gemstone with a natural colored gemstone having similar color characteristics such that a relatively course color comparison may be made between the natural colored gemstone and said handle portion of said simulated gemstone, and a relatively fine color comparison may be made between the natural gemstone and said gemstone body portion of said simulated gemstone.

17. A kit as in claim 16, wherein said gemstone body portion resembles a brilliant cut natural gemstone.

18. A kit as in claim 17, wherein said handle portion terminates in a disc-like member.

19. A kit as in claim 18, wherein said one-piece unitary structure includes said gemstone body and handle portions, and said disc-like member.

20. A kit as in claim 16 or 19, wherein said one-piece structure is molded from a methacrylic resin having an index of refraction of about 1.49.

21. A kit as in claim 16, wherein said handle is substantially planar.

22. A kit as in claim 16, wherein said tray includes a bed for receiving and positionally retaining said simulated gemstones therewithin.

23. A kit as in claim 22, wherein said bed includes:

a number of retaining elements for positionally retaining a corresponding number of said simulated gemstones, said retaining elements each including an opposing pair or recesses, wherein one of said recesses is sized and configured to accept therewithin said gemstone body portion so as to positionally retain the same, and the other of said recesses is in registry with a free end of said handle portion which is opposite said gemstone body portion, and wherein said free end of said handle portion may be pushed towards a bottom of said other recess to responsively cause said gemstone body portion to pivot upwardly away from said bed of said tray, whereby said gemstone body portion may be grasped and removed from said tray.

24. A kit as in claim 23, wherein said retaining elements of said bed further include a fulcrum surface against which a corresponding portion of said handle portion bears for assisting in the upward pivoting of said gemstone body portion in response to the free end of said handle portion being pushed towards a bottom of said other recess.

* * * * *